United States Patent
Herrera

(10) Patent No.: US 10,433,719 B1
(45) Date of Patent: Oct. 8, 2019

(54) MEDICAL DEVICE WARMER

(71) Applicant: Edward Herrera, Brooklyn, NY (US)

(72) Inventor: Edward Herrera, Brooklyn, NY (US)

( * ) Notice: Subject to any disclaimer, the term of this patent is extended or adjusted under 35 U.S.C. 154(b) by 543 days.

(21) Appl. No.: 15/090,731

(22) Filed: Apr. 5, 2016

(51) Int. Cl.
*A61B 1/12* (2006.01)
*A61B 50/30* (2016.01)
*A61B 50/00* (2016.01)
*A61B 18/00* (2006.01)

(52) U.S. Cl.
CPC ............. *A61B 1/128* (2013.01); *A61B 50/30* (2016.02); *A61B 2018/00041* (2013.01); *A61B 2050/0016* (2016.02); *A61B 2050/0072* (2016.02); *A61B 2050/3004* (2016.02)

(58) Field of Classification Search
CPC . A61B 1/128; A61B 50/30; A61B 2050/0016; A61B 2050/0072; A61B 2050/3004; A61B 2050/3006; A61B 2050/314; A61B 2050/316; A61B 2050/318; A61B 46/23; A61B 201/00005; A61B 201/00041; A61B 1/00138
USPC ........................ 206/363, 370, 438
See application file for complete search history.

(56) References Cited

U.S. PATENT DOCUMENTS

| | | | |
|---|---|---|---|
| 4,412,531 A * | 11/1983 | Chikashige | A61B 1/00068 600/104 |
| 5,351,675 A * | 10/1994 | Brodsky | A61B 1/127 126/263.08 |
| 5,366,492 A | 11/1994 | Ueki | |
| 5,910,106 A | 6/1999 | Morgan | |
| 6,886,553 B2 | 5/2005 | Yim | |
| 7,537,563 B2 | 5/2009 | Temple | |
| D609,357 S | 2/2010 | Yim | |
| 2002/0022762 A1 * | 2/2002 | Beane | A61B 1/122 600/101 |
| 2010/0270295 A1 | 10/2010 | Wang | |
| 2015/0101616 A1 * | 4/2015 | Wiley | A61B 19/10 128/852 |

FOREIGN PATENT DOCUMENTS

WO    2005096916 A1    10/2005
WO    2015051098 A1    4/2015

* cited by examiner

Primary Examiner — Aaron B Fairchild

(57) ABSTRACT

The medical device warmer is adapted for use with endoscopes. Specifically, the medical device warmer is a mechanical apparatus that is adapted to store and warm an endoscope during an endoscopic procedure. The medical device warmer is provisioned as a support kit. The support kit contains the medical device warmer as well as associated equipment and materials required for an endoscopic procedure. During an endoscopic procedure the support kit is clipped with a plurality of clips to the surgical draping used in the procedure to allow medical personnel ready access to the equipment. The medical device warmer comprises a warming cylinder, a cap and a support kit.

6 Claims, 5 Drawing Sheets

MEDICAL DEVICE WARMER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical devices, more specifically, a heating device that is adapted for the medical or therapeutic treatment of the human body.

Summary of Invention

The medical device warmer is adapted for use with endoscopes. Specifically, the medical device warmer is a mechanical apparatus that is adapted to store and warm an endoscope during an endoscopic procedure. The medical device warmer is provisioned as a support kit. The support kit contains the medical device warmer as well as associated equipment and materials required for an endoscopic procedure. During an endoscopic procedure the support kit is clipped with a plurality of clips to the surgical draping used in the procedure to allow medical personnel ready access to the equipment.

These together with additional objects, features and advantages of the medical device warmer will be readily apparent to those of ordinary skill in the art upon reading the following detailed description of the presently preferred, but nonetheless illustrative, embodiments when taken in conjunction with the accompanying drawings.

In this respect, before explaining the current embodiments of the medical device warmer in detail, it is to be understood that the medical device warmer is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the medical device warmer.

It is therefore important that the claims be regarded as including such equivalent construction insofar as they do not depart from the spirit and scope of the medical device warmer. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
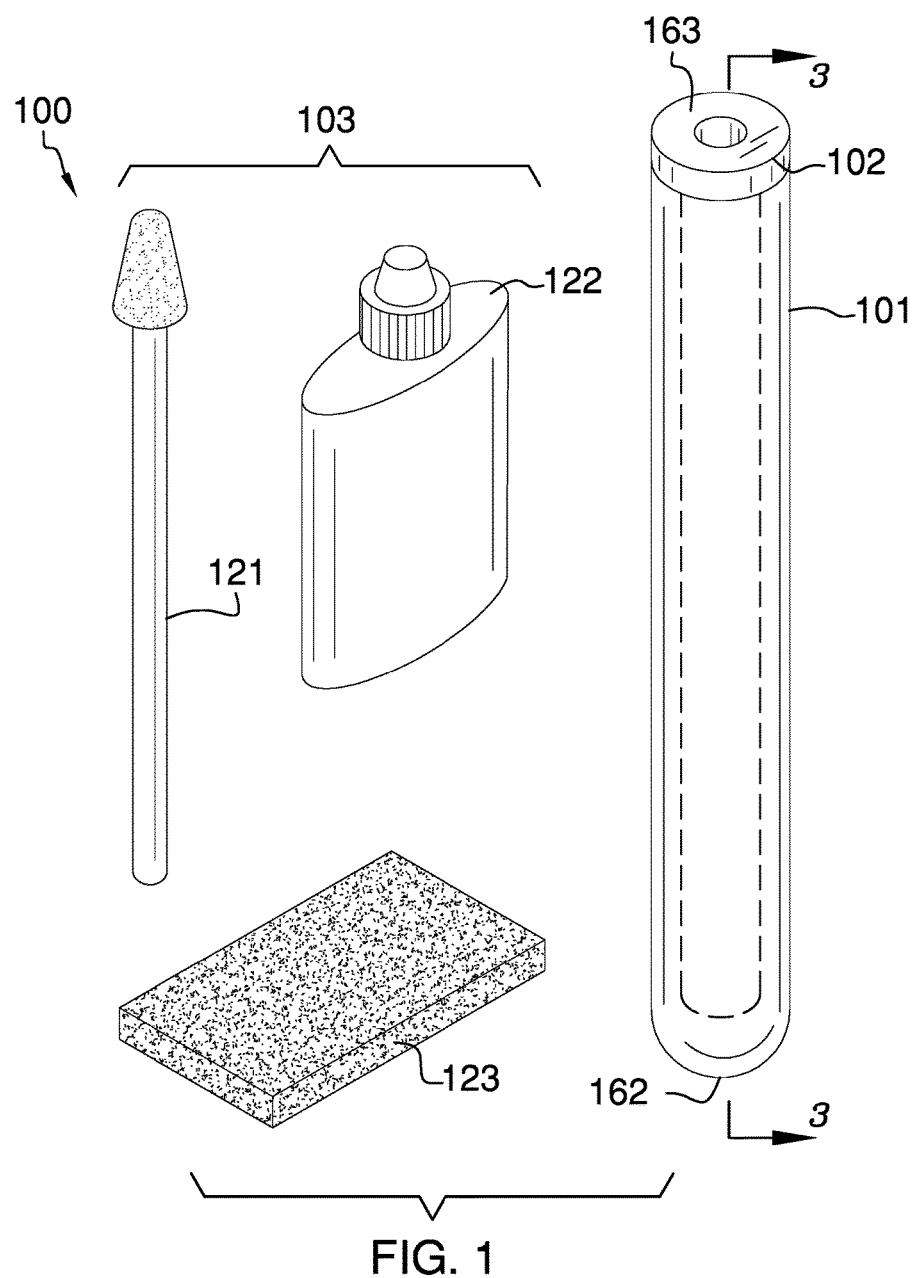
FIG. 1 is a perspective view of an embodiment of the disclosure.
Figure 2:
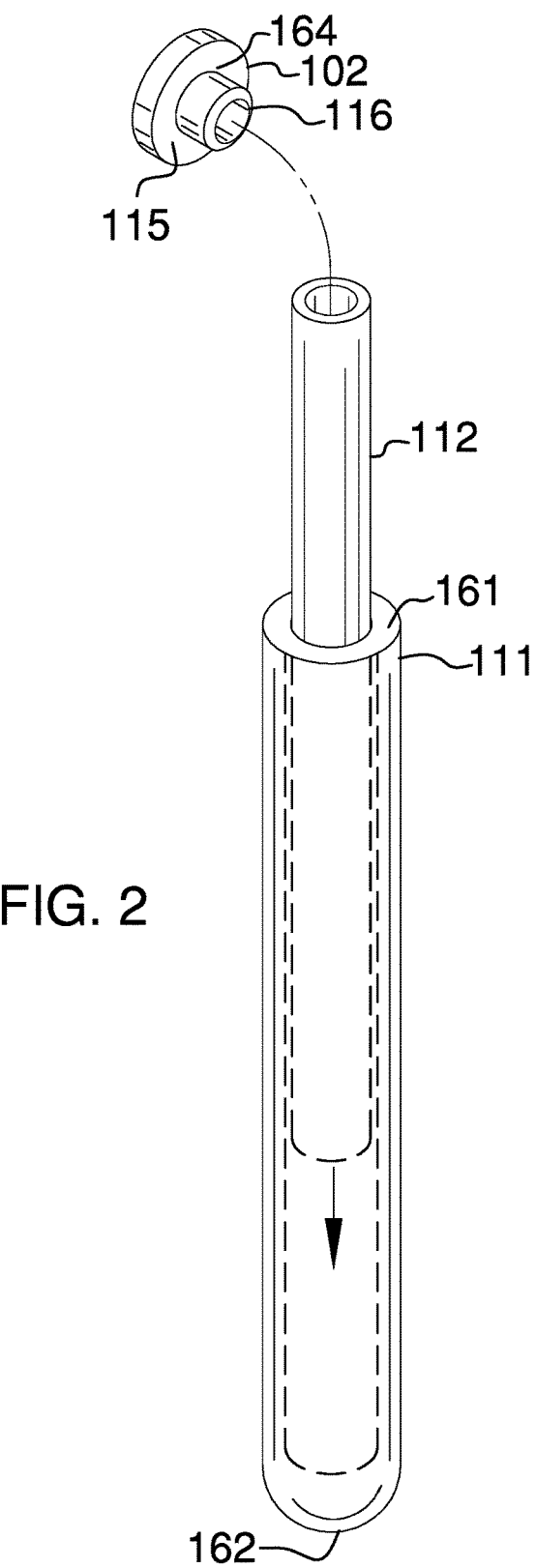
FIG. 2 is an exploded view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 5.

The medical device warmer 100 (hereinafter invention) comprises a warming cylinder 101, a cap 102 and a support kit 103. The invention 100 is adapted for use with endoscopes 131. Specifically, the invention 100 is a mechanical apparatus that is adapted to store and warm an endoscope 131 during an endoscopic procedure. The invention 100 is provisioned with a support kit 103. The support kit 103 contains the warming cylinder 101 and the cap 102 as well as associated equipment and materials required for an endoscopic procedure. During the endoscopic procedure the support kit 103 is clipped with a plurality of clips 125 to surgical draping 132 used in the procedure to allow medical personnel ready access to the equipment and materials contained within the invention 100.

The warming cylinder 101 further comprises a capped tube 111, a heat storage tube 112 and a wicking sponge 113. The warming cylinder 101 is further defined with a first end 161 and a second end 162. As shown most clearly in FIG. 3, the capped tube 111 provides the exterior containment of the warming cylinder 101. The capped tube 111 is closed at the second end 162. The heat storage tube 112 is a tube that is formed from a material with a high heat capacity that allows the heat storage tube 112 to store a relatively large amount of heat that will be transferred to the endoscope 131. The inner diameter of the heat storage tube 112 is sized such that it is larger than the outer diameter of the endoscope 131 thus allowing the endoscope 131 to be stored within the heat storage tube 112.

The warming cylinder 101 is designed such that the span of the outer diameter of the heat storage tube 112 is lesser than the span of the inner diameter of the capped tube 111. This allows the heat storage tube 112 to be removed from the capped tube 111 for sterilization as well as for the initial heating of the heat storage tube 112 before use of the invention 100. The heating of the heat storage tube 112 is discussed elsewhere in this disclosure. As shown most clearly in FIG. 3, the wicking sponge 113 is inserted into the closed end of the capped tube 111 during use. The purpose of the wicking sponge 113 is to wick unwanted liquids away from the endoscope 131. The wicking sponge 113 is replaceable and is disposed of after each endoscopic procedure.

In the first potential embodiment of the disclosure, the warming cylinder 101 is formed from plastic. Plastic is preferred over metal because of its superior insulating qualities. Suitable materials for the heat storage tube 112 include, but are not limited to, carbon fiber or ceramic based materials. Carbon fiber materials with a heat capacity of greater than 1.0 Joules per gram-degree Centigrade is preferred in the first potential embodiment of the disclosure.

The cap 102 is a cork like device that is used to seal the first end 151 of the warming cylinder 101. The cap 102 comprises a disk 115 and a plunger 116. The disk is a circular disk that is further defined with a first surface 163 and a second surface 164. The plunger 116 is a cylindrical projection that projects out of the second surface of the disk 115. As shown most clearly in FIG. 3, the outer diameter of the plunger 116 is less (under compression which is discussed later in this paragraph) than the inner diameter of the heat storage tube 112 thus allowing the cap 102 to seal the warming cylinder 101 and trap the heat of the heat storage tube 112 within the warming cylinder 101 when the invention 100 is not storing an endoscope 131. The plunger 116 is formed from an elastomeric material, which compresses when the plunger 116 is inserted into the heat storage tube 112.

The support kit 103 comprises a trocar wipe 121, anti-fog solution 122, a cleaning sponge 123, a mesh bag 124, and a plurality of clips 125. The trocar wipe 121, the anti-fog solution 122, the cleaning sponge 123, the plurality of clips 125 as well as the warming cylinder 101 and cap 102 are stored with mesh bag 124 while the invention 100 is awaiting use. The trocar wipe 121 is a commercially available cleaning tool that is used to clean the lens of the endoscope 131. The anti-fog solution 122 is a readily and commercially available chemical that is applied using the trocar wipe 121 to the lens of the endoscope 131. The cleaning sponge 123 is a sponge that is used to clean the exterior of the endoscope 131 during the endoscopic procedure. The plurality of clips 125 are readily and commercially available clips that are used to attach the mesh bag 124 to surgical draping 132. The mesh bag 124 is a readily and commercially available bag that is used to organize and store the invention 100.

Figure 3:
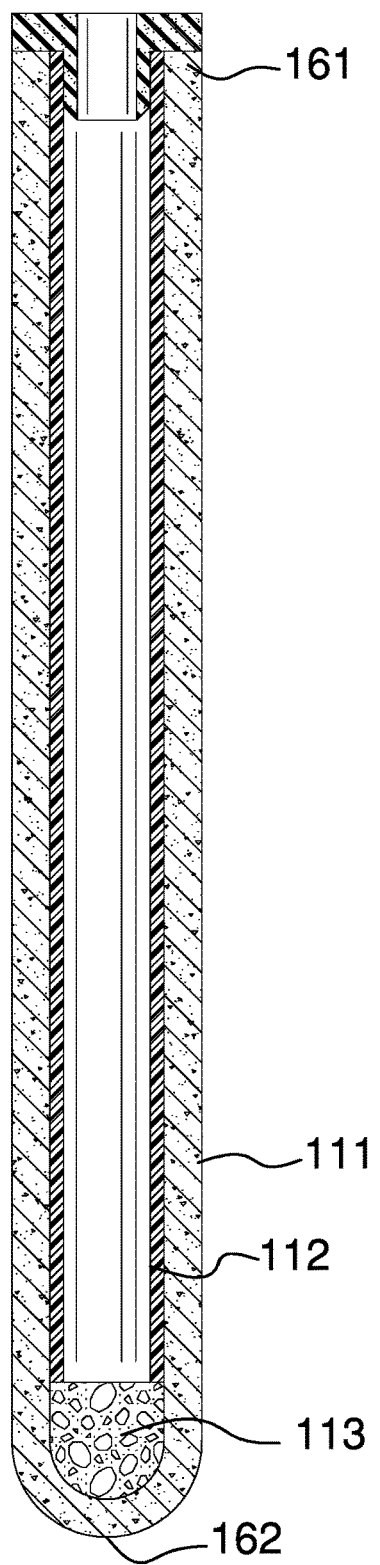
FIG. 3 is a cross-sectional view of an embodiment of the disclosure across 3-3 as shown in FIG. 1.
Figure 4:
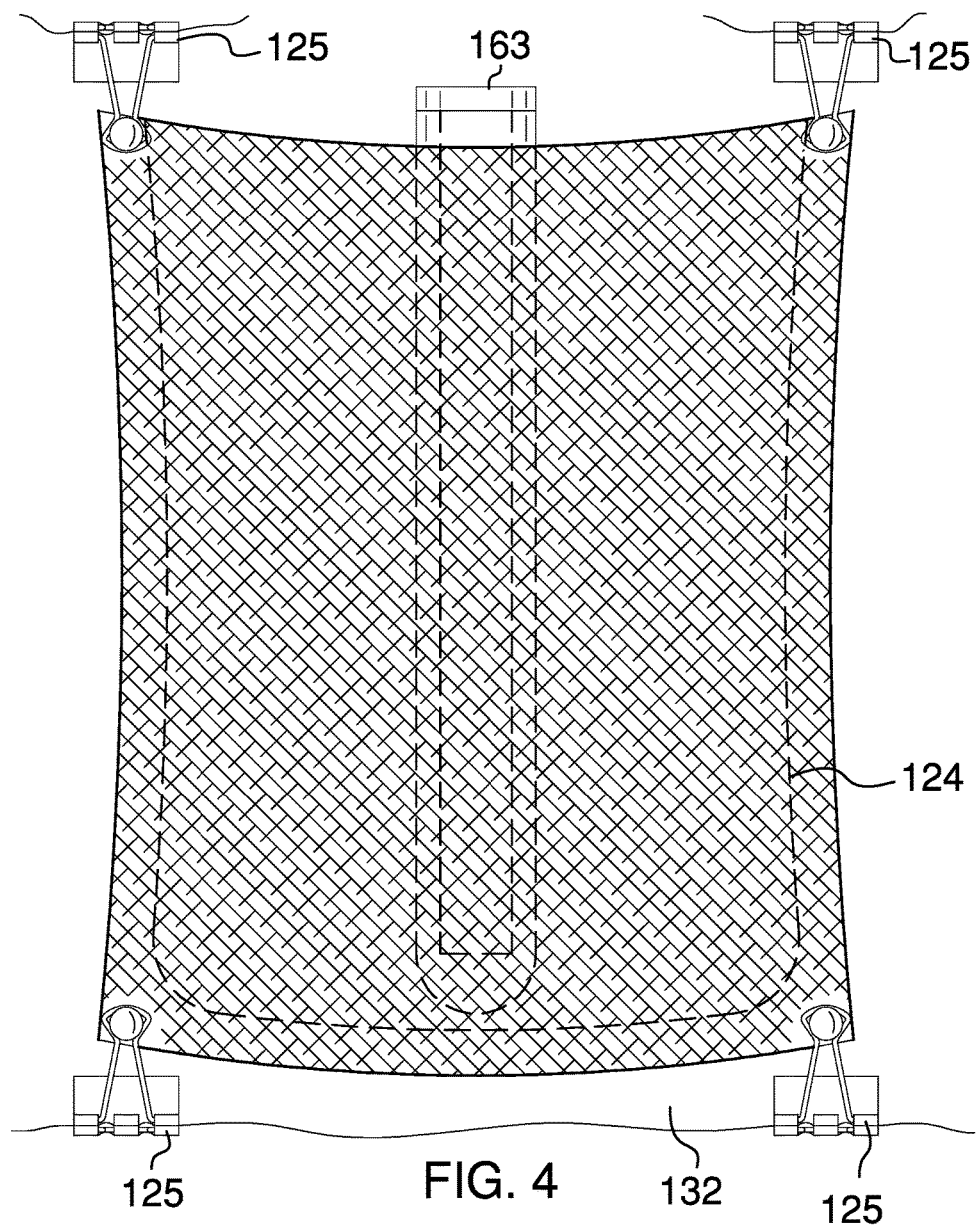
FIG. 4 is an in use view of an embodiment of the disclosure.
Figure 5:
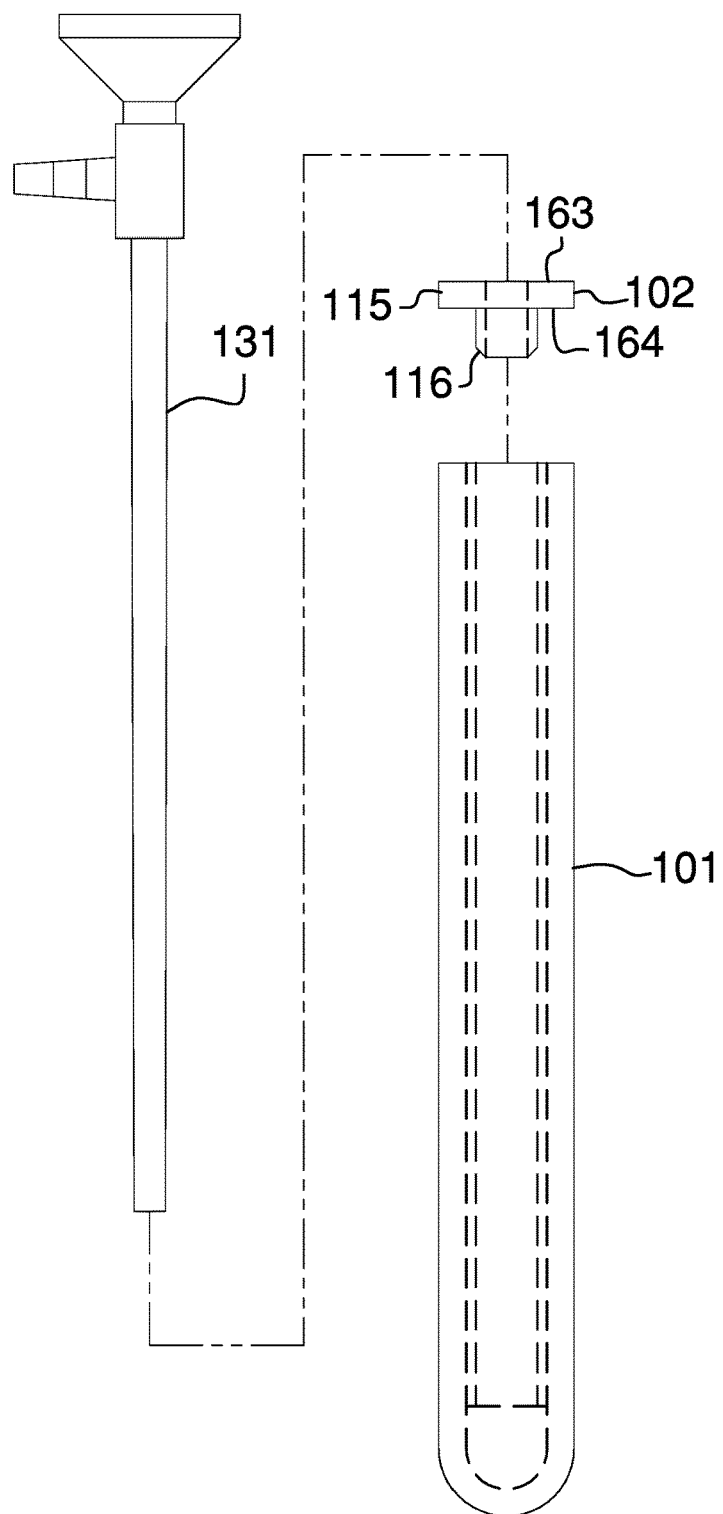
FIG. 5 is an in use view of an embodiment of the disclosure.

Before use of the first potential embodiment of the disclosure, the capped tube 111, the heat storage tube 112 and the cap 102 are sterilized in an autoclave type device. The capped tube 111, the heat storage tube 112 and the cap 102 are allowed to return to room temperature. Before use, the heat storage tube 112 is reheated in an oven or an autoclave type device. While the heat storage tube 112 is being reheated, the wicking sponge 113 is placed into the capped tube 111 such that the wicking sponge 113 is positioned at the second end 162 of the warming cylinder 101. This is shown most clearly in FIG. 3. Once the heat storage tube 112 has reached temperature, the heat storage tube 112 is placed into the capped tube 111. The capped tube 111 is then closed using the cap 102. The clearest depiction of the contents of this paragraph is shown in FIG. 3.

The following definitions were used in this disclosure:

Capped Tube: As used in this disclosure, a capped tube is a tube with one closed end and one open end.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; or, 4) the point, pivot, or axis around which something revolves.

Center Axis: As used in this disclosure, the center axis is the axis of a cylinder or cone like structure. When the center axes of two cylinder or like structures share the same line they are said to be aligned. When the center axes of two cylinder like structures do not share the same line they are said to be offset.

Cylinder: As used in this disclosure, a cylinder is a geometric structure defined by two identical flat and parallel ends that are circular in shape and connected with a single curved surface wherein when the cross section of the cylinder remains the same from one end to another. The axis of the cylinder is formed by the straight line that connects the center of each of the two identical flat and parallel ends of the cylinder. In this disclosure, the term cylinder specifically means a right cylinder which is defined as a cylinder wherein the curved surface perpendicularly intersects with the two identical flat and parallel ends.

Diameter: As used in this disclosure, a diameter of an object is a straight line segment that passes through the center of an object. The line segment of the diameter is terminated at the boundary of the object through which the line segment of the diameter runs.

Disk: As used in this disclosure, a disk is a cylindrically shaped object that is flat is appearance.

Drape: As used in this disclosure, to drape means to arrange in a fabric in flowing lines and folds.

Elastic: As used in this disclosure, an elastic is a material or object that deforms when a force is applied to it and that is able to return to its original shape after the force is removed. A material that exhibits these qualities is also referred to as an elastomeric material.

Inner Diameter: As used in this disclosure, the term inner diameter is used in the same way that a plumber would refer to the inner diameter of a pipe.

Outer Diameter: As used in this disclosure, the term outer diameter is used in the same way that a plumber would refer to the outer diameter of a pipe.

Tube: As used in this disclosure, a tube is a hollow rigid cylindrical device that is used for transporting liquids and gasses.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A medical device comprising:

a warming cylinder, a cap and a support kit;

wherein the medical device is adapted for use with endoscopes;

wherein the medical device is a mechanical apparatus that is adapted to store and warm an endoscope during an endoscopic procedure;

wherein the support kit contains the warming cylinder, the cap and associated equipment and materials required for an endoscopic procedure;

wherein the support kit is configured to be attached to surgical draping used in the endoscopic procedure;

wherein the warming cylinder comprises a capped tube, a heat storage tube and a wicking sponge;

wherein the warming cylinder is further defined with a first end and a second end;

wherein the warming cylinder is closed at the second end;

wherein the heat storage tube is formed from a material with a heat capacity of greater than 1.0 Joules per gram-degree Centigrade;

wherein a span of an inner diameter of the heat storage tube is greater than a span of an outer diameter of the endoscope;

wherein a span of an outer diameter of the heat storage tube is lesser than a span of an inner diameter of the capped tube;

wherein the wicking sponge is inserted into a second end of the capped tube;

wherein the wicking sponge is replaceable;

wherein the cap attaches to the first end of the warming cylinder;

wherein the cap comprises a disk and a plunger;

wherein the disk is further defined with a first surface and a second surface.

2. The medical device according to claim 1 wherein the plunger is a cylindrical projection that projects out of the second surface of the disk.

3. The medical device according to claim 2 wherein the plunger is made of an elastomeric material.

4. The medical device according to claim 3 wherein when placed under compression an outer diameter of the plunger is less than the inner diameter of the heat storage tube.

5. The medical device according to claim 4 wherein the support kit further includes a trocar wipe, anti-fog solution, a cleaning sponge, a mesh bag, and a plurality of clips.

6. The medical device according to claim 4 wherein the plurality of clips attach the mesh bag to the surgical draping.

* * * * *